US012579641B2

(12) United States Patent
Lee et al.

(10) Patent No.: US 12,579,641 B2
(45) Date of Patent: Mar. 17, 2026

(54) DEEP NEURAL NETWORK-BASED CEREBRAL HEMORRHAGE DIAGNOSIS SYSTEM

(71) Applicant: KYUNGPOOK NATIONAL UNIVERSITY INDUSTRY-ACADEMIC COOPERATION FOUNDATION, Daegu (KR)

(72) Inventors: Minho Lee, Daegu (KR); Joonho Chang, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 454 days.

(21) Appl. No.: 18/033,063

(22) PCT Filed: Oct. 19, 2021

(86) PCT No.: PCT/KR2021/014543
§ 371 (c)(1),
(2) Date: Apr. 20, 2023

(87) PCT Pub. No.: WO2022/086105
PCT Pub. Date: Apr. 28, 2022

(65) Prior Publication Data
US 2025/0378549 A1 Dec. 11, 2025

(30) Foreign Application Priority Data
Oct. 22, 2020 (KR) ......................... 10-2020-0137614

(51) Int. Cl.
G06T 7/00 (2017.01)
G16H 30/40 (2018.01)
G16H 50/20 (2018.01)

(52) U.S. Cl.
CPC ........... *G06T 7/0012* (2013.01); *G16H 30/40* (2018.01); *G16H 50/20* (2018.01);
(Continued)

(58) Field of Classification Search
CPC ......... G06T 7/0012; G06T 2207/20084; G06T 2207/30016; G06T 2207/10081;
(Continued)

(56) References Cited

U.S. PATENT DOCUMENTS 11,096,643 B2 * 8/2021 Takei ................... A61B 6/5294
11,164,067 B2 * 11/2021 Liang ................... G06V 10/764
(Continued)

FOREIGN PATENT DOCUMENTS

| KR | 10-2019-0087272 A | 7/2019 |
| KR | 10-2015224 B1 | 10/2019 |
| KR | 10-2125127 B1 | 6/2020 |
| KR | 10-2166441 B1 | 10/2020 |

OTHER PUBLICATIONS

U. Balasooriya and M. U. S. Perera, "Intelligent brain hemorrhage diagnosis using artificial neural networks," 2012 IEEE Business, Engineering & Industrial Applications Colloquium (BEIAC), Kuala Lumpur, Malaysia, 2012, pp. 128-133, doi: 10.1109/BEIAC.2012.6226036 (Year: 2012).*
(Continued)

*Primary Examiner* — Courtney Joan Nelson
(74) *Attorney, Agent, or Firm* — Bridgeway IP Law Group, PLLC; Sang Ho Lee; Hyun Woo Shin

(57) ABSTRACT
Provided is a deep neural network-based cerebral hemorrhage diagnosis system including: an input unit which receives a CT image and presents bleeding areas and sus-
(Continued)

pected bleeding areas; a bleeding size classification unit which is provided with the bleeding areas and suspected bleeding areas presented by the input unit and classifies the bleeding areas and suspected bleeding areas by size; a decoding unit which decodes the bleeding areas and suspected bleeding areas, classified by size by the bleeding size classification unit, by applying neural networks of different depth according to the size of the bleeding areas and suspected bleeding areas; and an output unit which sums and outputs, as a final bleeding area, the results decoded according to size by the decoding unit.

6 Claims, 2 Drawing Sheets

(52) U.S. Cl.
CPC ............... *G06T 2207/10081* (2013.01); *G06T 2207/20084* (2013.01); *G06T 2207/30016* (2013.01)

(58) Field of Classification Search
CPC . G06T 2207/20081; G06T 2207/30101; G06T 2207/10072; G06T 5/60; G16H 50/20; G16H 30/40; G16H 10/60; G16H 30/20; G16H 30/00; G16H 50/30; G16H 70/60; G06N 3/08; G06N 3/045; G06N 3/0464; G06N 20/00; A61B 6/501; A61B 6/032; A61B 6/5217; A61B 6/504; A61B 6/5205; A61B 5/4064; A61B 5/0042; A61B 2576/00; A61B 2576/026; A61B 5/7264; A61B 6/03; G06V 10/82; G06V 10/764; G06V 10/26; G06V 2201/03; G06V 10/25
See application file for complete search history.

(56) References Cited

U.S. PATENT DOCUMENTS

| | | | |
|---|---|---|---|
| 2019/0019304 A1 * | 1/2019 | Takei | .................... G06T 7/0012 |
| 2020/0027237 A1 | 1/2020 | Baumgartner et al. | |
| 2020/0090328 A1 * | 3/2020 | Takei | .................... G06T 7/0012 |
| 2020/0218961 A1 | 7/2020 | Kanazawa et al. | |

OTHER PUBLICATIONS

Kai Hu, Kai Chen, Xizhi He, Yuan Zhang, Zhineng Chen, Xuanya Li, Xieping Gao, Automatic segmentation of intracerebral hemorrhage in CT images using encoder-decoder convolutional neural network, Information Processing & Management, vol. 57, Issue 6, 2020, 102352, ISSN 0306-4573 (Year: 2020) https://doi.org/10.1016/j.ipm.2020.102352 (Year: 2020).*

Kwon, Doyoung et al., "Siamese U-net with healthy template for accurate segmentation of intracranial hemorrhage", Medical Image Computing and Computer Assisted Intervention—MICCAI 2019, Lecture Notes in Computer Science (LNIP), vol. 11766, pp. 848-855, 2019.

Hu, Kai et al., "Automatic segmentation of intracerebral hemorrhage in CT images using encoder-decoder convolutional neural network", Information Processing and Management, Jul. 12, 2020, pp. 1-16, vol. 57, No. 6, Article No. 102352.

Hssayeni, Murtadha D. et al. "Intracranial Hemorrhage Segmentation Using Deep Convolutional Model", arXiv:1910.08643v2. Nov. 15, 2019, Retrieved from <https://arxiv.org/pdf/1910.08643.pdf>, pp. 1-18.

Kim, Jonghong et al., "Convolutional Neural Network with Biologically Inspired Retinal Structure", Procedia Computer Science, Jul. 16-19, 2016, pp. 145-154, vol. 88.

Chang, Joonho et al., "PESA R-CNN: Perihematomal Edema Guided Scale Adaptive R-CNN for Hemorrhage Segmentation", IEEE Journal of Biomedical and Health Informatics, Jan. 2023, pp. 397-408.

* cited by examiner

DEEP NEURAL NETWORK-BASED CEREBRAL HEMORRHAGE DIAGNOSIS SYSTEM

TECHNICAL FIELD

The present invention relates to a deep neural network-based cerebral hemorrhage diagnosis system, and more particularly, to a deep neural network-based cerebral hemorrhage diagnosis system which finds all bleeding areas or areas having various sizes suspected of being bleeding areas in brain CT images together, performs a diagnosis by applying neural networks having different depths according to the bleeding areas having different sizes and the suspected bleeding areas, and has adaptability to the bleeding area sizes.

BACKGROUND ART

In general, cerebral hemorrhage causes damage to the brain due to bleeding in cerebral blood vessels. When areas damaged due to bleeding are not identified, patients may suffer from great harm, so a quick and accurate diagnosis is required.

Conventionally, the diagnosis of cerebral hemorrhage was diagnosed by doctors through CT images. In this case, the cerebral hemorrhage shown through the CT images has various sizes and shapes and blurring or the like occurs depending on resolutions of the CT images, and each doctor may diagnose bleeding differently in certain cases.

For this reason, there is a problem that normal areas are sometimes misdiagnosed as bleeding areas, and bleeding that occurs is sometimes not identified.

In order to solve these problems, medical image analysis using a deep learning-based image recognizer has been actively researched recently, and the use of the deep learning-based image recognizer is increasing in real situations, but the deep learning-based image recognizer still has low detection accuracy and cannot easily cope with cerebral hemorrhage having various shapes and sizes. Therefore, the development of a model to solve these problems is required.

DISCLOSURE

Technical Problem

The present invention is directed to providing a deep neural network-based cerebral hemorrhage diagnosis system capable of very accurately determining cerebral hemorrhage by finding all bleeding areas or areas having various sizes suspected of being bleeding areas in brain CT images together, performing a diagnosis by applying neural networks having different depths according to the bleeding areas of different sizes and the suspected bleeding areas, and having adaptability to the bleeding area sizes.

Technical Solution

One aspect of the present invention provides a deep neural network-based cerebral hemorrhage diagnosis system, including: an input unit configured to receive a CT image and present a bleeding area and a suspected bleeding area; a bleeding area size classification unit configured to receive the bleeding area and suspected bleeding area presented by the input unit and classify the received bleeding area and suspected bleeding area by size; a decoding unit configured to apply neural networks having different depths to the bleeding area and suspected bleeding area classified by size by the bleeding area size classification unit to perform decoding; and an output unit configured to combine results decoded by size in the decoding unit and output the combined decoded results as a final bleeding area.

The CT image transmitted to the input unit may be transmitted through a bleeding and suspected bleeding area detection network configured based on a U-Net model.

The bleeding and suspected bleeding area detection network may use a center surround difference method of finding a portion having a conspicuous difference by comparing a central portion and a peripheral portion of a kernel while applying the kernel to the CT image.

The input unit may focus on the bleeding area and the suspected bleeding area and present the focused bleeding area and suspected bleeding area in the form of a box.

The bleeding area size classification unit may classify the bleeding area and the suspected bleeding area by size through a size of the box focused on the bleeding area and the suspected bleeding area.

When outputting the decoded results to the final bleeding area, the output unit may classify a class through the decoded result of the entire bleeding area from the decoding unit, generate a bleeding area box, and apply the class and bleeding area box as the final bleeding area to output the final bleeding area.

Advantageous Effects

A deep neural network-based cerebral hemorrhage diagnosis system according to an embodiment of the present invention can very accurately diagnose bleeding by finding all bleeding areas or areas having various sizes suspected of being bleeding areas in brain CT images together and performing a diagnosis by applying neural networks having different depths according to the bleeding areas having different sizes and the areas suspected of being bleeding areas.

In addition, the deep neural network-based cerebral hemorrhage diagnosis system according to an embodiment of the present invention can be used for medical imaging in various areas without being limited to the cerebral hemorrhage.

In addition, the deep neural network-based cerebral hemorrhage diagnosis system according to an embodiment of the present invention can have practicability and versatility by performing a diagnosis with excellent performance regardless of the type of bleeding, such as intracerebral hemorrhage or subarachnoid hemorrhage, and prevent misrecognition of normal tissues by extracting and detecting only a bleeding-related area.

MODES OF THE INVENTION

Hereinafter, the description of the present invention with reference to the drawings is not limited to specific embodiments, and various modifications and/or embodiments may be applied. In addition, the content described below should be understood to include all modifications, equivalents, or substitutes included in the spirit and scope of the present invention.

In the following description, terms such as "first" and "second" are used to describe various components, but do not limit the meaning per se, and are used only for the purpose of distinguishing one component from another.

Like reference numbers used throughout this specification indicate like elements.

In the present invention, singular forms include plural forms unless the context clearly indicates otherwise. Further, it will be further understood that the terms "comprise" or "have" used below specify the presence of stated features, steps, operations, components, or parts mentioned in this specification, or a combination thereof, but do not preclude the presence or addition of one or more other features, numerals, steps, operations, components, parts, or a combination thereof.

The terms "unit," "-or/-er," "module," and the like used in the present disclosure mean units of processing at least one function or operation and may be implemented by hardware or software or a combination of hardware and software.

Hereinafter, a deep neural network-based cerebral hemorrhage diagnosis system according to an embodiment of the present invention will be described in detail with reference to the accompanying drawings.

Figure 1:
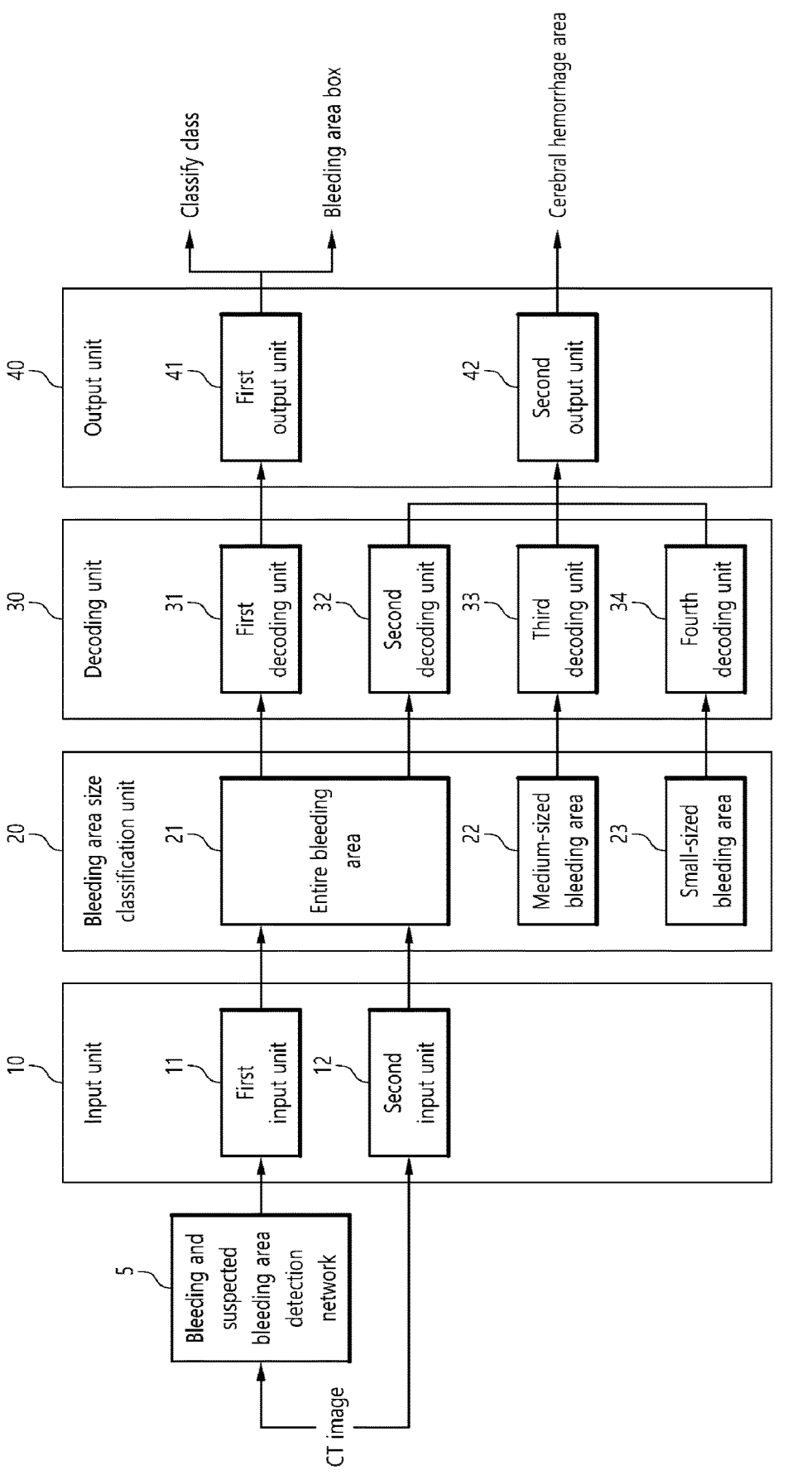
FIG. 1 is a block diagram illustrating a configuration of a deep neural network-based cerebral hemorrhage diagnosis system according to an embodiment of the present invention.
Figure 2:
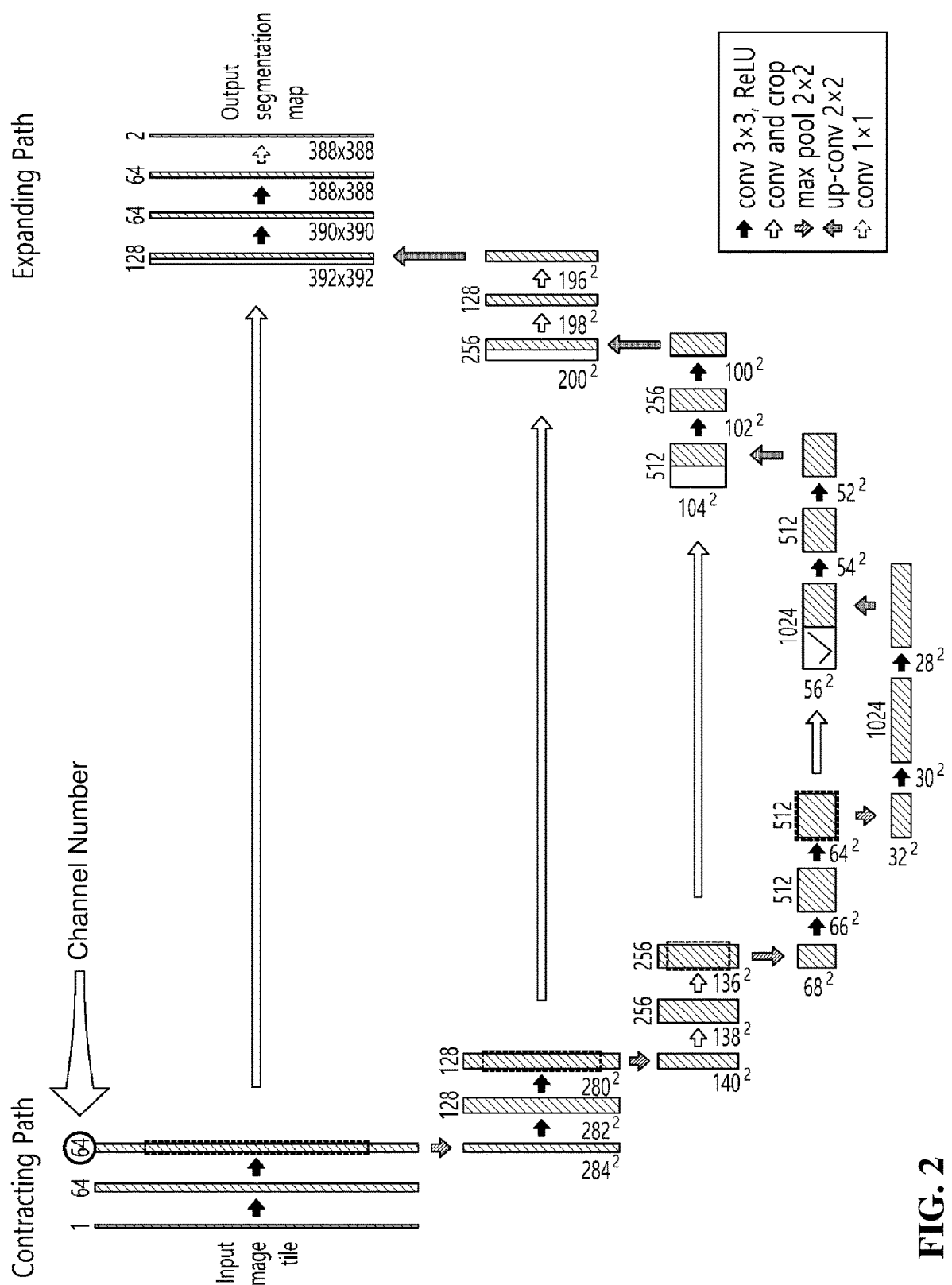
FIG. 2 is an exemplary diagram of a U-Net model.

FIG. 1 is a block diagram illustrating a configuration of a deep neural network-based cerebral hemorrhage diagnosis system according to an embodiment of the present invention, and FIG. 2 is an exemplary diagram of a U-Net model.

Referring to FIGS. 1 and 2, the deep neural network-based cerebral hemorrhage diagnosis system according to an embodiment of the present invention may be configured to include an input unit 10, a bleeding area size classification unit 20, a decoding unit 30, and an output unit 40.

Specifically, the input unit 10 may be linked with a CT imaging device (not illustrated) to receive a CT image generated during imaging by the CT imaging device. Here, the CT image has a difference in shade, and thus may be divided into normal areas and bleeding areas, and the input unit 10 of the present invention may detect and present suspected bleeding areas, which are formed in a smaller size and shape and are not clearly distinguished, along with bleeding areas.

More specifically, the CT image may have bleeding areas having various sizes and shapes distinguished from the normal areas by the difference in shade. Here, areas having a large size and shape may be reliably determined as bleeding areas, but areas having a small size and shape may be bleeding areas, but it is not easy to determine because the areas may be normal areas, but may be areas that look like bleeding areas due to a decrease in resolution, etc., and thus are not clearly distinguished.

For this reason, the input unit 10 of the present invention detects and presents not only the bleeding areas having a large size but also suspected bleeding areas that are not clearly distinguished due to their small size, thereby increasing the accuracy of a final bleeding area in the future.

In this case, there may be various methods of detecting a bleeding area and a suspected bleeding area, but according to the present invention, it is possible to detect the bleeding area and suspected bleeding area through a bleeding and suspected bleeding area detection network 5 configured based on a U-Net model.

That is, the CT image transmitted to the input unit 10 of the present invention is transmitted through the bleeding and suspected bleeding area detection network 5 configured based on the U-Net model.

Specifically, the U-Net model is a network drawn in a U-shape as illustrated in FIG. 2, with one side forming an encoding area and the other side forming a decoding area, and in the encoding area, a contracting path may be formed, and in the decoding area, an expanding path may be formed.

In the contracting path, a convolution process that captures characteristics of the CT image by applying a kernel (or filter) and a pooling process that fills a blank due to a reduced size in the convolution process are performed to downsample a feature map and capture contexts, which are relationships between neighboring image pixels, and in the expanding path, upsampling is performed to increase a resolution that decreases due to the downsampling in the contracting path.

In other words, in the contracting process, the convolution process and the pooling process are performed, and thus, in each operation, the number of channels of the feature map doubles, but the size of the feature map is downsampled by a factor of two, and in the expanding path, the size of the feature map is reduced little by little by the convolution process, but the number of channels is reduced by a factor of two through the upsampling, and the size of the feature map is doubled and thus the feature map become wider and thinner again.

In this process, in order to solve the problem of missing data between an input image and an output image caused by performing the convolution process without the padding process of filling the reduced blanks, after repeatedly performing a copy and corp process of mirroring an empty portion of an image from an image of the corresponding contracting path during the expanding path at each operation, a 1×1 convolution operation is performed in the last layer to change the number of channels of feature vectors to two channels, thereby mapping each feature vector according to the required number of classes.

The U-Net model may increase the processing speed of the deep neural network-based cerebral hemorrhage diagnosis system of the present invention and improve the determination accuracy by resolving a trade-off between context recognition and localization.

Moreover, the bleeding and suspected bleeding area detection network 5 of the present invention, which is configured based on the U-Net model as described above, uses a center surround difference method of comparing a central portion and a peripheral portion of the kernel while applying the kernel (or filter) to the CT image to find a portion having a conspicuous difference, thereby detecting conspicuous features having a conspicuous difference.

Specifically, the center surround difference method, which is a method of comparing the central portion and peripheral portion of the kernel while moving the kernel as much as the specified strides to find the portion having the conspicuous difference, follows [Equation 1] below as a method of reducing a basic image step by step to $\frac{1}{2}$, $\frac{1}{22}$ ($\frac{1}{4}$), and $\frac{1}{28}$ ($\frac{1}{256}$), respectively, to realize an image pyramid, interpolating an image having a large scale into a final scale, and subtracting pixels from each other.

$$I(c, s) = |I(c)\theta I(s)| \qquad \text{[Equation 1]}$$

$$C \in \{2, 3, 4\}, \delta \in \{3, 4\}$$

$$s = c + \delta$$

Here, I(c, s) refers to the output of the equation, representing the conspicuous difference found by comparing two different scales of an image. I(c) represents the image at scale 'c', which corresponds to the central portion being compared. I(s) represents the image at scale 's', which corresponds to the peripheral portion being compared. The variable δ represents an offset used to determine the value of 's'. The value of 'c' may be 2, 3, or 4, and the value of 'δ' may be 3, or 4. The symbol 'θ' represents the operation of subtracting pixels between the two images, I(c) and I(s).

By applying the U-Net model to which the center surround difference method has been applied, it is possible to extract features with a conspicuous difference, and to detect not only the bleeding areas but also the suspected bleeding area which has different characteristics from the normal areas, to minimize missed parts.

Unlike the conventional models that detect bleeding through the entire image including information unrelated to the bleeding, the input unit 10, which receives the CT image that has passed through the bleeding and suspected bleeding area detection network 5 as described above, may focus only on a region of interest, that is, areas determined as the bleeding area and the suspected bleeding area, and present the region of interest to the bleeding area size classification unit 20 in the box shape.

In this way, the present invention has the advantage of greatly improving the accuracy of detection by preventing misrecognition of normal areas as bleeding areas and not missing even small bleeding areas.

Meanwhile, the input unit 10 described above is configured to include a first input unit 11 and a second input unit 12, and the first input unit 11 may detect the bleeding area and suspected bleeding area through the CT image and present an area requiring diagnosis, and the second input unit 12 may extract features from the CT image and transmit the extracted features to the bleeding area size classification unit 20.

That is, the bleeding area size classification unit 20 may perform classification by bleeding area size by applying the bleeding area and suspected bleeding area presented in the first input unit 11 to the entire CT image feature extracted in the second input unit 12.

The bleeding area size classification unit 20 may receive the bleeding area and suspected bleeding area presented by the input unit 10 and classify the received bleeding area and suspected bleeding area by size. In this case, the bleeding area size classification unit 20 may classify the bleeding area and suspected bleeding area by various sizes according to the setting, but may preferably be set to classify the bleeding areas into three sizes.

For example, as illustrated in the drawing, the bleeding area and suspected bleeding area may be divided into an entire bleeding area 21, a medium-sized bleeding area 22, and a small-sized bleeding area 23. Here, the distinction between the medium and small sizes depends on the user's setting.

Here, the bleeding area size classification unit 20 may measure and classify the sizes of the bleeding area and suspected bleeding area presented by the input unit 10 in various ways, but when the bleeding area and suspected bleeding area are preferably presented in the box shape by the input unit 10, the bleeding area and suspected bleeding area may be easily classified by size through the size of the box.

The decoding unit 30 may perform decoding by applying a neural network having different depths according to the size of the bleeding area and suspected bleeding area classified by size by the bleeding area size classification unit 20.

That is, the decoding unit 30 may have a plurality of decoding units as the bleeding area size classification unit 20 classifies the bleeding area and the suspected bleeding area by size. In this case, the plurality of decoding units 30 may prepare the number of decoding units corresponding to n+1 in preparation for the number n of sizes classified by the bleeding area size classification unit 20. This is to share the function of the output unit 40 to be described below.

For example, when the bleeding area size classification unit 20 performs classification by three sizes, the decoding unit 30 may include the first to fourth decoding units 31 to 34, that is, four decoding units.

Here, applying the neural network at different depths according to the size of the bleeding area or suspected bleeding area in each decoding unit 31 to 34 involves changing the number of hidden layers of each neural network, when the bleeding area size is small, decoding a shallow layer to prevent loss of information when the decoding process becomes deep, and obtaining a high resolution result to minimize missing areas, and when the bleeding area size is large, obtaining low resolution results a by decoding a deep layer, but more information may be obtained.

Through this, when all suitable decoding of different depths is merged and applied in the output unit 40 to be described later, it is possible to minimize the loss of each bleeding area result and more accurately detect the bleeding areas of various sizes and shapes.

When the conventional models apply only one type of decoding, in the case of the deep decoding, there is a high possibility of losing small bleeding area information, and in the case of the shallow decoding, much bleeding area information is not obtained, which is in sharp contrast to the problem of not obtaining high accuracy.

The output unit 40 may combine the decoded results by size in the decoding unit 30 and output the combined decoded results as the final bleeding area. In this case, the output unit 40 may simply combine the results and output the combined results as the final bleeding area, but preferably, when outputting the combined results as the final bleeding area, the output unit 40 may classify classes through the decoded result of the entire bleeding area from the decoding unit 30, generate the bleeding area box, and apply the classes and bleeding area box as the final bleeding area to output the final bleeding area.

To this end, the output unit 40 may be configured to include a first output unit 41 that is responsible for classifying the classes and generating the bleeding area box and a second output unit 42 that outputs the final bleeding area, and may combine the information of the first output unit 41 and the second output unit 42 so that the information is easily checked.

The deep neural network-based cerebral hemorrhage diagnosis system according to the embodiment of the present invention described above may very accurately detect and diagnose the bleeding areas having various sizes.

In addition, the deep neural network-based cerebral hemorrhage diagnosis system according to an embodiment of the present invention has been described with regard to the example of cerebral hemorrhage for better understanding, but may also be used in medical imaging in various areas.

Although exemplary embodiments of the present invention have been described with reference to the accompanying drawings, those skilled in the art will appreciate that various modifications and alterations may be made without departing from the spirit or essential features of the present invention. Therefore, the embodiments described above are illustrative in all respects and are not restrictive.

DESCRIPTION OF REFERENCE SIGNS

5: Bleeding and suspected bleeding area detection network
10: Input unit
20: Bleeding area size classification unit
30: Decoding unit
40: Output unit

The invention claimed is:

1. A deep neural network-based cerebral hemorrhage diagnosis system, comprising:
   an input processor configured to receive a CT image and identify a bleeding area and a suspected bleeding area;
   a bleeding area size classification processor configured to receive the bleeding area and the suspected bleeding area identified by the input processor and classify the received bleeding area and the suspected bleeding area by size;
   a decoding processor configured to apply neural networks having different depths to the bleeding area and the suspected bleeding area classified by size by the bleeding area size classification processor to perform decoding; and
   an output processor configured to combine results decoded by size by the decoding processor and output the combined decoded results as a final bleeding area.

2. The deep neural network-based cerebral hemorrhage diagnosis system of claim 1, wherein the CT image is transmitted to the input processor through a bleeding and suspected bleeding area detection network configured based on a U-Net model.

3. The deep neural network-based cerebral hemorrhage diagnosis system of claim 2, wherein when applying a kernel to the CT image, the bleeding and suspected bleeding area detection network uses a center surround difference method to find a portion having a difference greater than a predetermined value by comparing a central portion and a peripheral portion of the kernel.

4. The deep neural network-based cerebral hemorrhage diagnosis system of claim 1, wherein the input processor focuses on the bleeding area and the suspected bleeding area and identifies the focused bleeding area and the suspected bleeding area using a form of a box.

5. The deep neural network-based cerebral hemorrhage diagnosis system of claim 4, wherein the bleeding area size classification processor classifies the bleeding area and the suspected bleeding area by size based on a size of the box focused on the bleeding area and the suspected bleeding area.

6. The deep neural network-based cerebral hemorrhage diagnosis system of claim 1, wherein, when outputting the combined decoded results of the final bleeding area, the output processor classifies a class based on the combined decoded results for an entire bleeding area from the decoding processor, generates a bleeding area box, and applies the class and the bleeding area box to the final bleeding area to output the final bleeding area.

* * * * *